United States Patent
Kunishi et al.

(10) Patent No.: US 8,474,656 B2
(45) Date of Patent: Jul. 2, 2013

(54) VISCOUS MATERIAL EXTRUDING DISPENSER

(75) Inventors: Hideto Kunishi, Kurashiki (JP); Yasujiro Ohara, Tokyo (JP); Katsuhito Kuwahara, Tokyo (JP); Toru Toma, Tokyo (JP); Satoshi Sakamoto, Tokyo (JP)

(73) Assignees: Kuraray Noritake Dental Inc., Kurashiki-shi (JP); Yoshino Kogyosho Co., Ltd., Tokyo (JP)

( * ) Notice: Subject to any disclaimer, the term of this patent is extended or adjusted under 35 U.S.C. 154(b) by 1151 days.

(21) Appl. No.: 12/309,108

(22) PCT Filed: Jun. 25, 2007

(86) PCT No.: PCT/JP2007/062725
§ 371 (c)(1),
(2), (4) Date: Feb. 6, 2009

(87) PCT Pub. No.: WO2008/007536
PCT Pub. Date: Jan. 17, 2008

(65) Prior Publication Data
US 2009/0289084 A1 Nov. 26, 2009

(30) Foreign Application Priority Data
Jul. 13, 2006 (JP) .................. 2006-192775

(51) Int. Cl.
*B67D 1/16* (2006.01)
(52) U.S. Cl.
USPC ........... 222/108; 222/326; 222/386; 222/494; 222/571; 600/576; 604/222; 604/228

(58) Field of Classification Search
USPC .................. 600/576, 578; 604/208–209, 246, 604/218–219, 221–222, 228–229; 222/108, 222/326–327, 386–386.5, 391, 491–494, 222/522–523, 566–574
See application file for complete search history.

(56) References Cited

U.S. PATENT DOCUMENTS 3,976,068 A * 8/1976 Lundquist .................. 604/518
4,373,535 A * 2/1983 Martell ...................... 600/578
(Continued)

FOREIGN PATENT DOCUMENTS

EP 0 117 498 A1 9/1984
EP 1 285 675 A1 2/2003
(Continued)

OTHER PUBLICATIONS

Mar. 2, 2012 Search Report issued in the European Patent Application No. 07767531.2-2318.
(Continued)

*Primary Examiner* — Paul R Durand
*Assistant Examiner* — Andrew P Bainbridge
(74) *Attorney, Agent, or Firm* — Oliff & Berridge, PLC

(57) ABSTRACT

A syringe has a dripless feature by using an O-ring located between a conical disc and a flat plunger disc in an annular groove on a moving plunger. The flat plunger disc has a series of projections that offset the o-ring off the flat plunger disc surface when the plunger is not actuated. When the plunger is actuated, the o-ring distorts to rest on the projections and also on the surface of the flat plunger disc. When the plunger is released, the o-ring's resiliency pulls the o-ring back to its original shape which sucks back the fluid being dispensed so that no or less drips occur.

9 Claims, 7 Drawing Sheets

U.S. PATENT DOCUMENTS

| | | | | |
|---|---|---|---|---|
| 4,657,028 A | * | 4/1987 | Rich et al. | 600/578 |
| 4,852,772 A | * | 8/1989 | Ennis, III | 222/386 |
| 4,923,096 A | * | 5/1990 | Ennis, III | 222/391 |
| 5,314,416 A | * | 5/1994 | Lewis et al. | 604/219 |
| 6,447,610 B1 | | 9/2002 | Vetter | |
| 7,290,573 B2 | * | 11/2007 | Py et al. | 141/329 |

FOREIGN PATENT DOCUMENTS

| | | |
|---|---|---|
| JP | A-59-160467 | 9/1984 |
| JP | A-4-347151 | 12/1992 |
| JP | A-2001-57987 | 3/2001 |
| JP | A-2001-61962 | 3/2001 |
| JP | A-2006-158983 | 6/2006 |
| JP | A-2006-204628 | 8/2006 |

OTHER PUBLICATIONS

Feb. 28, 2012 Office Action issued in Japanese Patent Application No. 2006-192775 (with English Translation).

Apr. 15, 2013 Office Action issued in EP Application No. 07 767 531.2.

* cited by examiner

VISCOUS MATERIAL EXTRUDING DISPENSER

TECHNICAL FIELD

The present invention relates to a dispenser suitable for extruding various composites and/or other viscous materials used for dental treatment or the like, and intends to certainly prevent drips of contents from the tip of a nozzle.

RELATED ART

A paste material with high viscosity such as composite or an adhesive is often used for dental treatment or the like. A syringe type dispenser is typically used to extrude contents from a small diameter nozzle by pressing a plunger.

With this kind of dispenser, a plunger is operated to extrude contents filled therein usually in multiple stages (i.e. all contents are not extruded by a single operation), and the operation of the plunger is interrupted so as to shut off the extrusion of the contents. But even after the interruption, the pressing force applied to the plunger remains as residual pressure in a filling space of contents, so that the contents leak out of the tip of the nozzle, which makes it difficult to extrude the appropriate amount of the contents and makes it impossible to utilize the expensive contents without waste.

There has been proposed as a solution for the above problem an ejecting structure of a container for dental viscous material in which a groove bottom of a groove for arranging an O-ring has a shape gradually or stepwisely tapered toward the rear end of the container 1, and a distance between the groove bottom and the inner wall of the container at a the point apart from the farthest (rear) position from the nozzle in the nozzle (forward) side by 0.5 times of the diameter of the cross section of the O-ring under unloaded condition is set to be 0.85 times or more larger than the diameter of the cross section of the O-ring under unloaded condition (see, for example, JP2001-57987A). In the structure, torsion of O-ring is caused in pressing operation of the plunger by imposing appropriate resistance to the O-ring, and the plunger is displaced backwardly by a restoring force of the O-ring exerted after the interruption of the extruding of the contents, thereby preventing drips of contents.

With such ejecting structure, however, it is difficult to control the quality and to be controlled and perform efficient production since the size of the container is small and such structure requires high accuracy of numerical setting for components so as to cause O-ring torsion. During setting a plunger in a container, in addition, the O-ring arranged in a groove may be moved to a position farthest from the nozzle side in the groove by the resistance between the O-ring and the container and thus the O-ring torsion, during pressing the plunger, cannot be caused to prevent drips of contents from the tip of the nozzle.

DISCLOSURE OF THE INVENTION

An object of the invention is to propose a novel dispenser which can displace a plunger backward upon interrupting the extrusion of the contents and then certainly induce the accompanying suction effect (back suction) so as to prevent drips or leaks of contents. Another object of the invention is to propose a dispenser which can certainly discharge remaining air entrapped during filling of contents to prevent bubbles from mixing into the contents.

The invention provides a dispenser comprising a syringe body having a space for filling contents and equipped with an extruding nozzle at its front end, a plunger slid, by pressing force applied thereto, in the syringe body to extrude the contents in the filling space from the tip of the extruding nozzle, an O-ring placed in an annular groove formed in the front end section of the plunger and slidable on the inner wall surface of the syringe body, wherein the annular groove is formed as a defined recess having a flat bottom wall over its entirety; a plurality of projections or grooves are formed on the sidewall of the annular groove with intervals therebetween so that the side portion of the O-ring comes into contact with the sidewall, being elastically displaced and then compressively deformed upon pressing the plunger while the O-ring is restored upon releasing the load applied for pressing the plunger to slide the plunger is slid in a direction opposed to the pressing direction, thus inducing back suction of contents.

It is preferable that the syringe body is provided with a polygonal flange on its outer wall.

One or more ribs for discharging air with which the O-ring is in slidable contact are preferably provided on the front inner wall of the syringe body. It is more preferable that a step portion having a projection height smaller than the height of the rib is formed at the connecting portion between the rib and the inner wall of the syringe body. Furthermore, a projection or a rib can be formed on either one of the inner wall surface of the syringe body with which the front end of the plunger is in contact and the front end surface of the plunger, forming gaps between the inner wall of the syringe body and the front end of the plunger.

It is preferable that the plunger is a hollow cylindrical with the front end being closed and that openings are formed in the peripheral wall at least at opposed positions.

When the plunger is pressed to extrude the contents in the filling space, the O-ring comes into contact with a projection formed on the sidewall of the groove in the plunger and then embeds into the groove, being elastically displaced (the O-ring is displaced to wave shape in the adjacent area of the sidewall). When the plunger is further continued to be pressed from that state, the O-ring is compressively deformed so as to fill gaps between the sidewall of the groove and the O-ring deformed to wave shape. When the pressing of the plunger is interrupted and thus the load applied thereto is released, the O-ring is to restore to its original shape while maintaining its position in the syringe body, causing the plunger to slide, according to the amount of elastic displacement and compressive deformation, to the direction opposed to the press-in direction. This depressurizes the filling space and thus induces back suction in which contents in the extruding nozzle are drawn into the filling space.

The O-ring intrudes into gaps between projections or into grooves regardless of the depth of the grooves or the like, being elastically displaced and compressively deformed to wave shape over its entire circumference. Therefore, the back suction is certainly induced, thus preventing drips of contents from the tip of the nozzle.

A polygonal flange can be provided on the outer wall of the syringe body, thereby preventing a dispenser from rolling when placed.

One or more ribs for discharging air with which O-ring is in slidable contact are formed on the front inner wall of the syringe body. In addition, a projection or a rib can be formed on either one of the inner wall surface with which the front end of the plunger is in contact and the front end surface of the plunger, forming gaps between the inner wall of the syringe body and the front end of the plunger. Therefore, air remaining in dispenser during filling of the contents is certainly discharged through the gaps formed by the ribs, thus preventing bubbles from mixing into the contents.

A step portion having a projection height smaller than the height of the rib is formed at the connecting portion between the rib and the inner wall of the syringe body, preventing the occurrence of scratch on the seal surface of a molded article when the molded article is removed from the mold in a molding step.

The plunger is hollow cylindrical with its front end being closed and openings are formed in the peripheral wall at least at opposed positions. Such structure not only can prevent shrinkage in the groove in which O-ring is placed to stabilize the shape but also can hold a core through the openings from the cavity side to preclude offset of the core and thus prevent uneven thickness or defects of the plunger.

Figure 1:
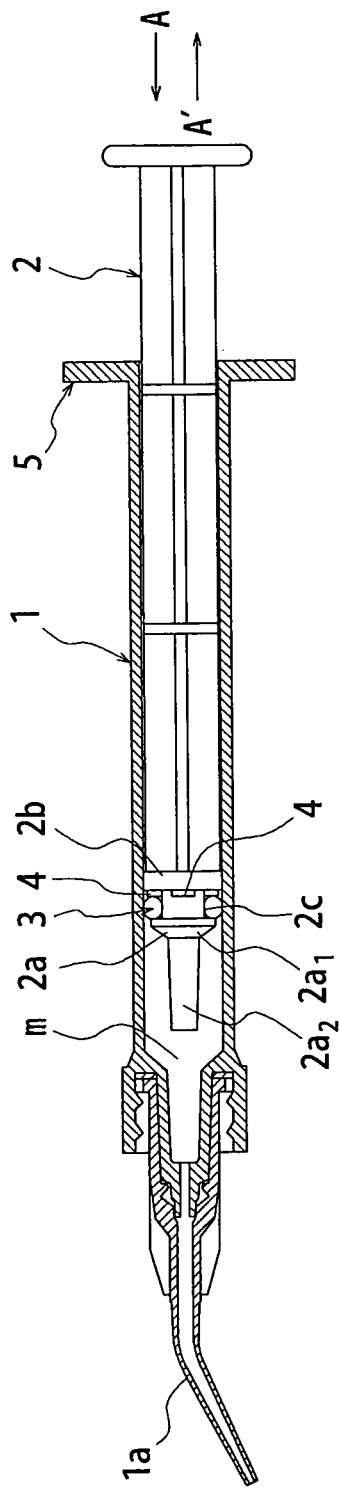
FIG. 1 shows an extruding dispenser according to one preferred embodiment of the present invention.

REFERENCE SYMBOLS 1 syringe body
1a extruding nozzle
2 plunger
2a conical disc
2b pressing disc
2c annular groove
3 O-ring
4 projection
5 flange
6 rib
7 opening

BEST MODE FOR CARRYING OUT THE INVENTION

Figure 2:
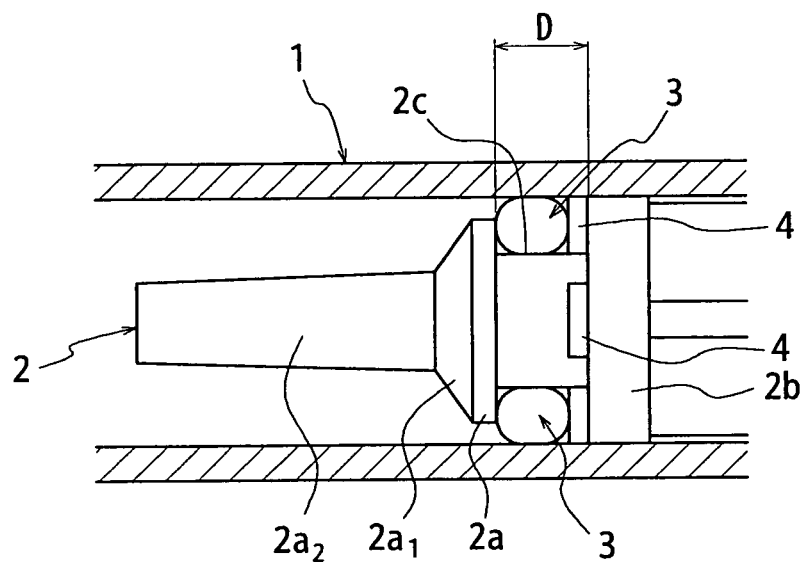
FIG. 2 is a cross-sectional view of a main portion of the dispenser shown in FIG. 1 under an unloaded condition.

The invention will be described more concretely with reference to the accompanying drawings. FIG. 1 shows a dispenser for filling a viscous material according to one preferred embodiment of the present invention, and FIG. 2 is an enlarged view of a main portion thereof.

Reference numeral 1 in the drawings designates a cylindrical syringe body whose front and rear ends are open. The syringe body 1 has a space m for filling contents therein and an extruding nozzle 1a is equipped to the front end of the filling space.

Reference numeral 2 designates a plunger slid in the syringe body 1 to extrude the contents in the filling space m from the tip of the extruding nozzle 1a. The plunger 2 is provided with a conical disc 2a and a pressing disc 2b at its front section, and an annular groove 2c having the width D is formed between the discs as a defined recess having a flat bottom wall over its entirety (see FIG. 2).

The conical disc 2a has a shape generally agree with the inner shape of the syringe body 1 so as to reduce the amount of the contents left after extruding out all contents in the syringe body 1, and is composed of a combination of a large-diameter disk portion $2a_1$ and a small-diameter slender disk portion $2a_2$.

Reference numeral 3 designates an O-ring placed in the groove 2c in the plunger 2 (when O-ring is set, there may be a gap in the groove 2c having the width D). The O-ring 3 is slidable on the inner wall surface of the syringe body 1 and seals the filling space m between the plunger 2 and the syringe body 1. In the illustrated embodiment, the O-ring 3 has an elliptically-deformed shape due to contact with the inner wall of the syringe body 1 when the plunger 2 is set in the syringe body 1. A material for the O-ring 3 may be appropriately selected from silicone rubber, synthetic rubber, butyl rubber, fluoro rubber or the like. In view of resistance to contents, however, silicon rubber is preferable to be used to form the O-ring 3.

Figure 3:
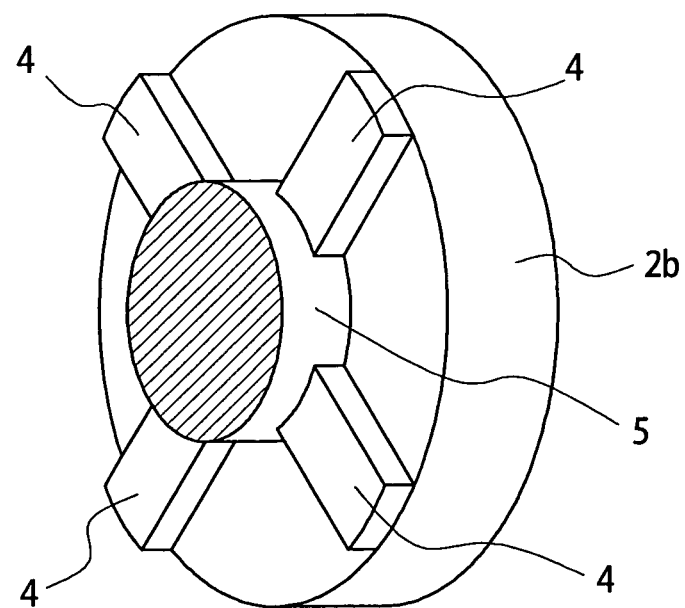
FIG. 3 is an external perspective view of a main portion of the dispenser shown in FIG. 1.

Reference numeral 4 designates projections (or grooves) provided, at 90° intervals, on the sidewall of the pressing disc 2b of the plunger 2, as shown in the external perspective view of FIG. 3. The projections 4 causes the O-ring 3 to be elastically displaced to wave shape, by its contact with the side of the O-ring 3 during press-in operation of the plunger 2, at the adjacent area of the sidewall and then compressively deformed so as to fill the gaps between the sidewall of the groove and the O-ring 3 deformed to wave shape. The plunger 2 is slid to the direction A' opposed to the press-in direction A by the restoring force of the O-ring 3 exerted by releasing the load for pressing the plunger 2, thus inducing back suction (see FIG. 1).

Furthermore, reference numeral 5 designates a flange on which fingers are placed upon pressing the plunger 2.

Figure 4:
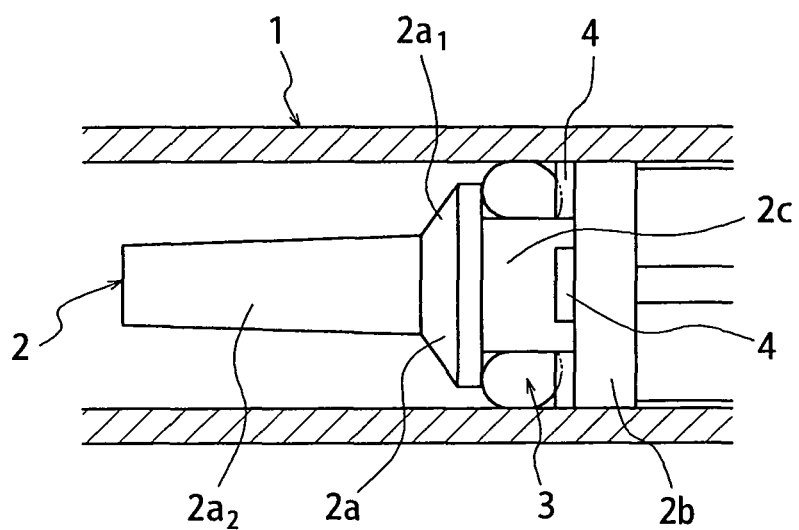
FIG. 4 is a cross-sectional view of a main portion of the dispenser shown in FIG. 1 under a loaded condition.
Figure 5A:
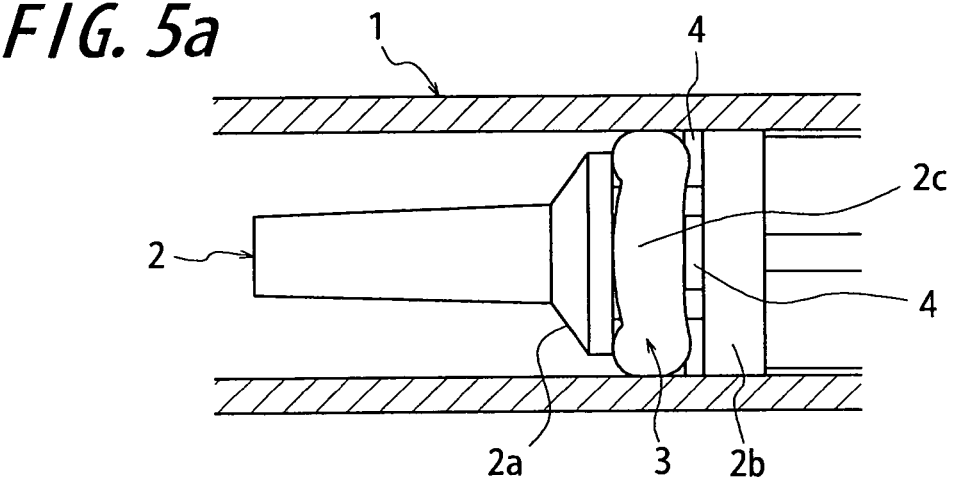
FIG. 5a is a schematic view showing a stage of displacement and deformation of an O-ring.
Figure 5B:
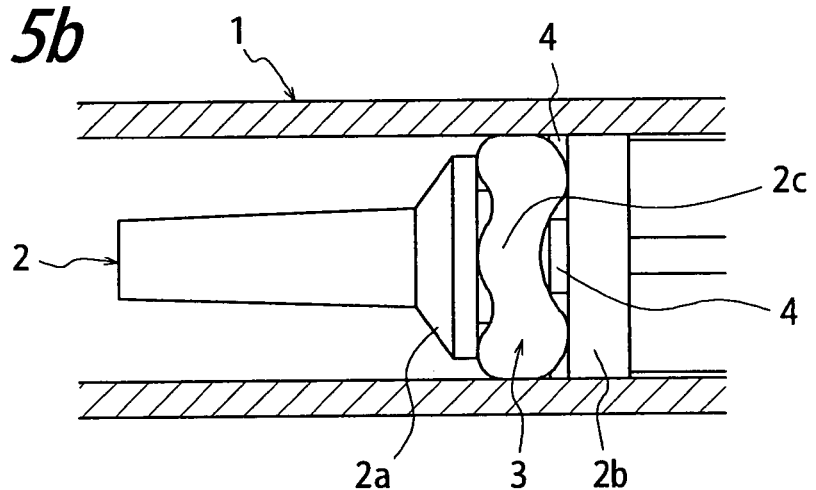
FIG. 5b is a schematic view showing a stage of displacement and deformation of an O-ring.

The O-ring 3 is in a state shown in FIG. 2 before pressing the plunger 2, i.e. under an unloaded condition. When the extruding of the contents begins by pressing the plunger 2, the O-ring 3 comes into contact with the projections 4 thus being elastically displaced, and then partially intrudes into gaps between projections 4 thus being displaced to wave shape, as shown in FIG. 4. The deformation states are schematically shown in FIGS. 5a, 5b and 5c.

Figure 5C:
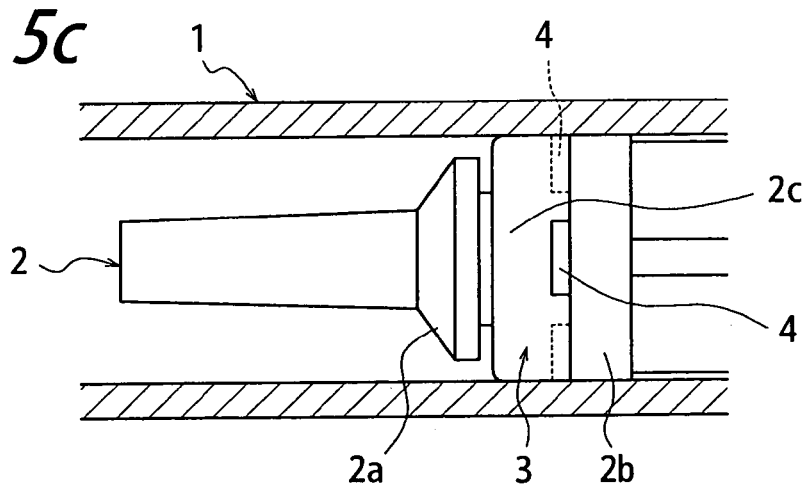
FIG. 5c is a schematic view showing a stage of displacement and deformation of an O-ring.

During extruding of contents, the O-ring 3 is initially in an elastically displaced state with a wave shape and eventually in a compressively deformed state shown in FIG. 5c which is a state where the gaps between the sidewall of the groove and the O-ring 3 deformed, in the previous stage, to wave shape are filled. Thereafter, when the press-in of the plunger 2 is interrupted to release the load applied thereto, the elastically displaced O-ring 3 is to restore to its original shape while maintaining its position in the syringe body. The plunger 2 is slid in the direction opposed to the press-in direction by the restoring force thus caused and negative pressure is generated in the syringe body 1 to draw the contents in the extruding nozzle 1a into the filling space m.

In the illustrative preferred embodiment of the invention, the projections 4 are provided as means for elastically displacing the O-ring 3, by way of example. This configuration is not particularly limited, and longitudinal ribs or grooves can be provided in place of the projections 4 to elastically displace the O-ring 3.

The flange 5 can be adopted to have a polygonal shape to prevent a dispenser from rolling when the dispenser is placed.

Figure 6:
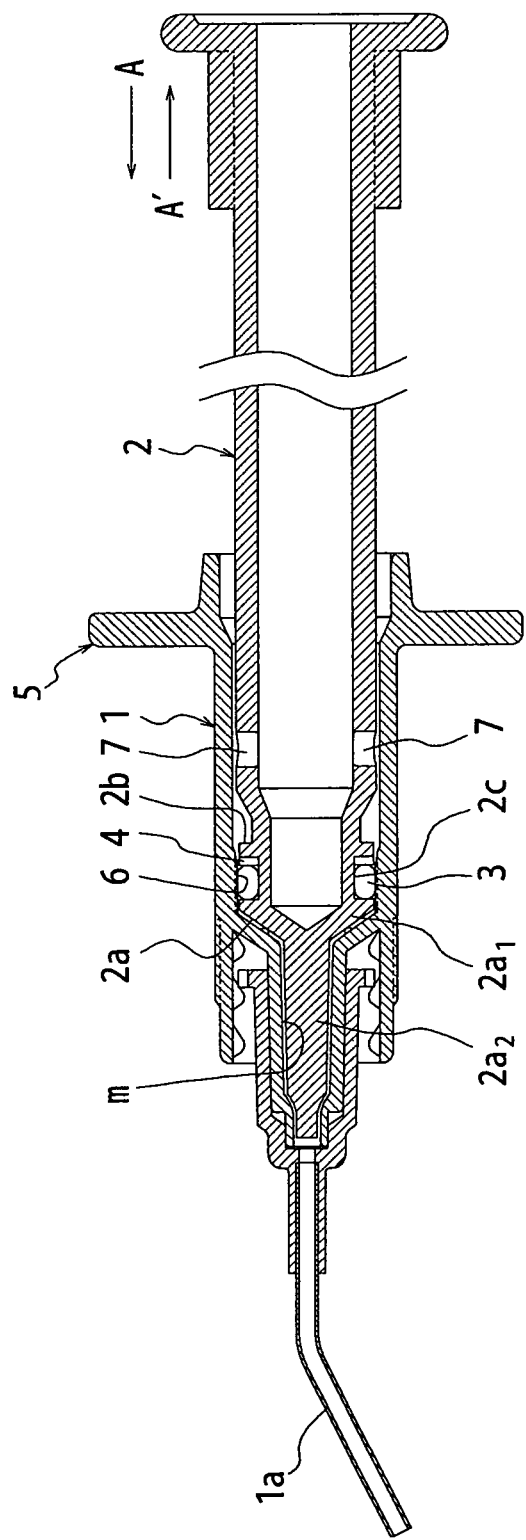
FIG. 6 shows an extruding dispenser according to another preferred embodiment of the present invention.
Figure 7:
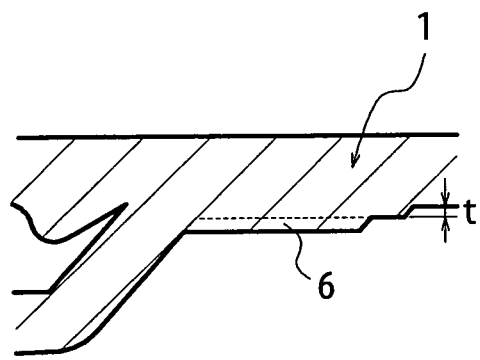
FIG. 7 is a cross-sectional view of a main portion (step portion) of the dispenser shown in FIG. 6.
Figure 8:
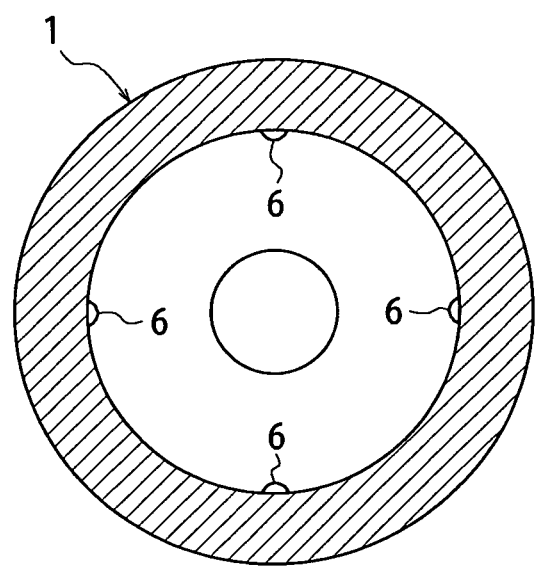
FIG. 8 is a cross-sectional view of a main portion of the dispenser shown in FIG. 6.
Figure 9:
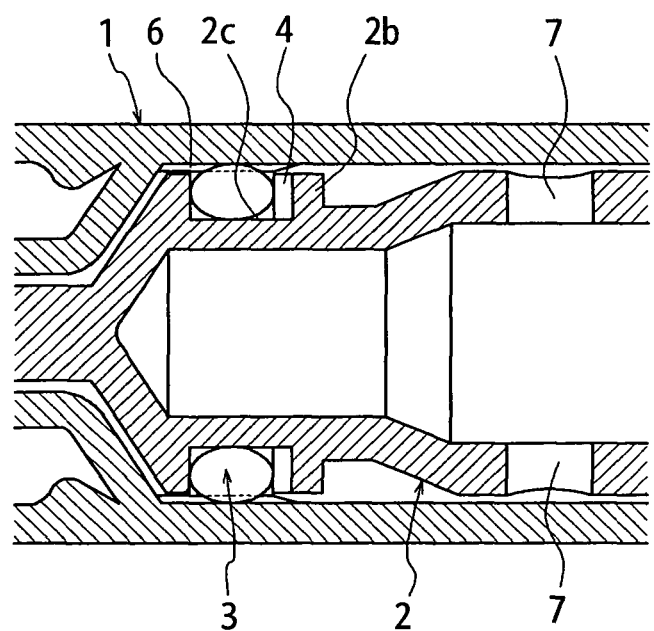
FIG. 9 is an enlarged cross-sectional view of a main portion of the dispenser shown in FIG. 6.

FIG. 6 shows a dispenser for extruding a viscous material according to another preferred embodiment of the present invention. FIGS. 7-9 are enlarged views of a main portion of the dispenser.

This embodiment illustrates the structure where four ribs 6 axially extending on the front inner wall of the syringe body 1 are circumferentially provided at even intervals (see FIG. 8). The rib 6 is arranged to be in slidable contact with the O-ring 3 in a state where the plunger 2 is at the side of the extruding nozzle 1a (i.e. a state where the plunger 2 is completely pressed-in in the syringe body 1). Furthermore, the ribs 6 at the open side of the syringe body 1 is arranged to be connected to the inner wall of the syringe body 1 via the step portion t (see FIG. 7).

When contents are filled into the filling space m, the plunger 2 is located at the forefront of the syringe body 1 and the O-ring 3 is arranged to be in slidable contact with the rib 6. In case that the extruding nozzle 1a is used to fill contents into the syringe body 1, air in the syringe body 1 cannot be completely discharged during filling of contents and may be mixed into the contents as bubbles, making it difficult to extrude the precise amount of contents due to the bubble. When the filling begins under the condition of the embodiment, however, the ribs 6 release the general state where the O-ring 3 and the inner wall of the syringe body 1 are sealed up by mutual contact, so that air in the syringe body 1 is discharged through gaps between ribs 6, preventing mixing of bubbles to the contents. Therefore, the above problem can be solved and thus the embodiment of the invention is considered preferable.

It is more preferable that a step portion t having a projection height smaller than the height of the rib 6 is formed at the connecting portion between the rib 6 and the inner wall surface of the syringe body 1, as shown in FIG. 7. The step portion t prevents the occurrence of scratch on the seal surface of the syringe body 1 when the syringe body 1 is removed from the mold in a molding step.

The plunger 2 is a hollow cylindrical with its front end being closed and openings 7 can be provided in the peripheral wall at least at opposed positions. The contents may leak out from the rear part of the syringe body 1 due to instability of the shape of the sealed portion. However, the hollow cylindrical shape of the plunger 2 prevents the occurrence of shrinkage in molding or at the sealed portion of the annular groove 2c or the like in which O-ring 3 is placed, thus allowing the stable sealing.

The openings 7 are also used to enable striking pins, which are distributed (or integrated) in a cavity upon molding the plunger 2, to abut on the core and thus hold the core from the cavity side, preventing offset of the core due to pressure in injection molding and thus precluding uneven thickness or defects of the molded plunger 2. Furthermore, the openings 7 serve as exhaust passages for remaining air entrapped during filling of contents.

The placement of the O-ring 3 in the plunger 2 and the operation thereof are the same as the above FIGS. 1-5.

As a material for syringe body 1 or plunger 2, employed can be different kinds of thermoplastic resin such as polyolefins, polyesters, polyethers or polystyrenes. More specifically polypropen (PP) or polyethylene (PE) as polyolefin material; polyethylene terephthalate (PET) or polybutylene terephthalate (PBT) as polyester material; polyoxymethylene (POM) as polyether material; AS or BS as polystyrene resin can be cited as typical examples. Any of these materials can be appropriately selected depending on applications or contents to be filled. The above resins can also be used to the extruding nozzle 1. Alternatively, the extruding nozzle 1a with its tip made of metal can be also used (see FIG. 6).

INDUSTRIAL APPLICABILITY

The invention provides an extruding dispenser in which an operation load of a plunger is stable and contents of the dispenser do not leak out.

The invention provides an extruding dispenser certainly discharging remaining air entrapped in the dispenser during filling of contents to prevent mixing of bubbles to the contents and having excellent sealing capability to prevent leaks of contents.

What is claimed is:

1. A dispenser for extruding a viscous material, the dispenser comprising:
    a syringe body having a space for filling contents and equipped with an extruding nozzle at a front end thereof,
    a plunger that can slide in the syringe body by a pressing force applied thereto in order to extrude the contents in the filling space from a tip of the extruding nozzle,
    an O-ring placed in an annular groove formed in a front end section of the plunger and slidable on an inner wall surface of the syringe body, wherein the annular groove is formed as a recess having a flat bottom wall and defined by a conical disc that is arranged at a front end of the plunger and a pressing disc that is spaced backwardly from the conical disc, and wherein the O-ring contacts directly with the flat bottom wall, and
    a plurality of projections or grooves formed on the pressing disc at intervals therebetween so that a side portion of the O-ring comes into contact with the sidewall of the annular groove, is elastically displaced and then compressively deformed upon pressing and so that the O-ring is restored upon releasing a load applied for pressing the plunger to slide the plunger in a direction opposed to the pressing direction, thus inducing back suction of contents.

2. The dispenser for extruding the viscous material according to claim 1, wherein the syringe body has a polygonal flange on an outer wall thereof.

3. The dispenser for extruding the viscous material according to claim 1, wherein a front inner wall of the syringe body has one or more ribs for discharging air with which the O-ring is in slidable contact.

4. The dispenser for extruding the viscous material according to claim 3, wherein a connecting portion between the inner wall of the syringe body and the rib is provided with a step portion having a projection height smaller than a height of the rib.

5. The dispenser for extruding the viscous material according to claim 1, wherein either one of the inner wall surface of the syringe body with which the front end of the plunger is in contact and a front end surface of the plunger has a projection or a rib forming gaps between the inner wall of the syringe body and the front end of the plunger.

6. The dispenser for extruding the viscous material according to claim 1, wherein the conical disc has a diameter smaller than a diameter of the pressing disc.

7. The dispenser for extruding the viscous material according to claim 1, wherein the plunger is a hollow cylindrical body with a closed front end and openings in a peripheral wall at least at opposed positions.

8. The dispenser for extruding the viscous material according to claim 1, wherein a plurality of projections or grooves are not formed on the conical disc.

9. The dispenser for extruding the viscous material according to claim 1, wherein the plurality of projections are formed on the pressing disc, and a distance between adjacent projections of the plurality of projections is greater than a width of a projection of the plurality of projections.

* * * * *